United States Patent [19]

Meyers et al.

[11] Patent Number: 4,588,588
[45] Date of Patent: May 13, 1986

[54] ANTIBIOTIC EM5487

[75] Inventors: Edward Meyers, East Brunswick; Raymond Cooper, Old Bridge, both of N.J.

[73] Assignee: E. R. Squibb & Sons, Inc., Princeton, N.J.

[21] Appl. No.: 557,803

[22] Filed: Dec. 5, 1983

[51] Int. Cl.$^4$ ............... A61K 35/00; C12P 1/04
[52] U.S. Cl. ................................ 424/122; 435/170
[58] Field of Search ..................... 424/122; 435/170

[56] References Cited

U.S. PATENT DOCUMENTS 3,160,560  12/1964  De Boer et al. .................. 424/122
4,187,292  2/1980  Higeshide et al. ................ 424/122

OTHER PUBLICATIONS

American Type Culture Collection, Catalogue of Strains I, 15th Ed., p. 140, 1982.

Primary Examiner—Alvin E. Tanenholtz
Attorney, Agent, or Firm—Lawrence S. Levinson; Donald J. Barrack

[57] ABSTRACT

A novel antifungal antibiotic which has been designated EM5487 is prepared by cultivating *Lysobacter gummosus* A.T.C.C. No. 39472 under submerged aerobic conditions in an aqueous nutrient medium containing an assimilable carbohydrate and nitrogen source.

3 Claims, 4 Drawing Figures

INFRARED SPECTRUM OF EM5487 IN POTASSIUM BROMIDE

INFRARED SPECTRUM OF EM5487 IN POTASSIUM BROMIDE

100 MHz $^{13}$C NMR SPECTRUM OF EM5487 IN DEUTERATED METHANOL

400 MHz $^1$H NMR SPECTRUM OF EM5487 IN DEUTERATED METHANOL

ULTRAVIOLET SPECTRUM OF EM5487 IN METHANOL

ANTIBIOTIC EM5487

SUMMARY OF THE INVENTION

Cultivation of a strain of *Lysobacter gummosus* that has been deposited in the American Type Culture Collection as A.T.C.C. No. 39472, yields a novel antibiotic substance designated EM5487 having activity against yeasts and fungi.

DETAILED DESCRIPTION OF THE INVENTION

The Microorganism

Figure 1:
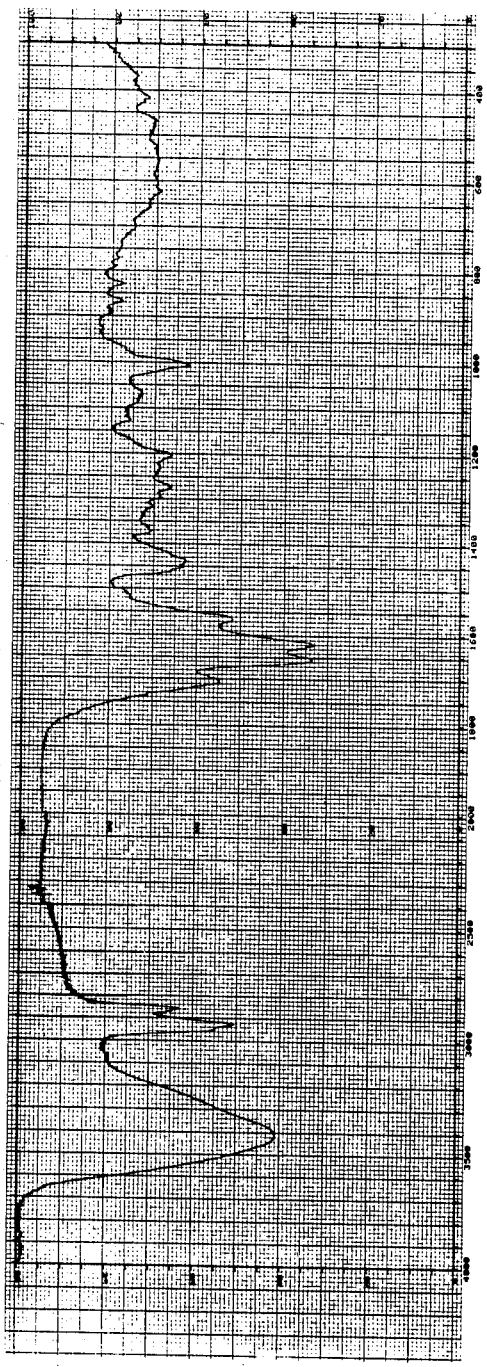
FIG. 1 shows the infrared spectrum of EM5487 in potassium bromide.

The microorganism used for the production of EM5487 is a strain of a *Lysobacter gummosus* isolated from the soil. A subculture of the organism can be obtained from the permanent collection of the American Type Culture Collection, Rockville, Md. Its accession number in the repository is A.T.C.C. No. 39472. In addition to the specific microorganism described and characterized herein, it should be understood that mutants of the microorganism (e.g., mutants produced through the use of x-rays, ultraviolet radiation or nitrogen mustards) can also be cultivated to produce EM5487.

For isolating and characterizing *Lysobacter gummosus*, a portion of a soil sample in which it is present is suspended in sterile diluent (e.g., water) and shaken. A dilution of this suspension is plated onto a nutrient medium, e.g., Triple Sugar Iron Agar (Baltimore Biological Laboratories, Cockeysville, Md.) that has been modified by the addition of vitamin B12 and cycloheximide. The composition of the medium used is:

|  | Grams |
| --- | --- |
| Polypeptone | 20.0 |
| NaCl | 5.0 |
| Lactose | 10.0 |
| Sucrose | 10.0 |
| Dextrose | 1.0 |
| Ferrous ammonium sulfate | 0.2 |
| Sodium thiosulfate | 0.2 |
| Phenol Red | 0.025 |
| Agar | 13.0 |
| Distilled water to one liter | |

The medium is sterilized in an autoclave at 121° C. for 15 minutes. After being allowed to cool to approximately 50°–55° C., the medium is supplemented with the following sterile solutions:

0.1% vitamin B solution: 2.0 ml.
1.0% solution of cycloheximide: 10.0 ml.

After 48 to 72 hours incubation at 25° C., colonies are isolated from the plated soil. These isolated colonies are then grown in a medium containing:

|  | Grams |
| --- | --- |
| Beef extract | 1.5 |
| Yeast extract | 3.0 |
| Peptone | 6.0 |
| Dextrose | 1.0 |
| Distilled water to one liter | |

The medium is autoclaved at 121° C. for 15 minutes.

The characteristics of *Lysobacter gummosus* species A.T.C.C. No. 39472 are:

Cell Morphology: The organism is a gram negative rod and by phase microscopy appears predominately as long, thin rods with rounded rather than tapered ends. Some chain formation is evident. On tryptone (0.05%)—yeast extract (0.05%) agar, the rods are bundled together with their longitudinal axes parallel to the direction of outgrowth, indicative of gliding motility. Slime trails have been observed on the agar.

Cultural Characteristics: Liquid cultures are quite viscous and agar cultures are quite mucilaginous. On sucrose—yeast extract agar (0.25% and 0.5%, respectively), the colonies are yellow and translucent with scalloped, colorless edges that are transparent and spreading in an irregular manner.

Biochemical Reactions: The organism is proteolytic, as evidenced by its clearing of the opaqueness of a skim milk, acetate agar. It produces catalase, oxidase, phosphates and is able to utilize citrate as the sole carbon source for growth. It does not produce a water soluble pigment nor does it hydrolyze starch. It is lipolytic on Tween 20 and Tween 80, and produces acid from glucose, cellobiose, sucrose (delayed), and lactose but not from glycerol or mannitol. It grows on eosin-methylene blue agar.

Physiology: The organism is lytic for yeast cells. The G+C content of its DNA is 66.9%, a value within the range of 65.4 to 70.1 mol % reported by Christensen and Cook.

These characteristics serve to identify the producer of EM5487 as *Lysobacter gummosus*, in agreement with the description of this organism by P. Christensen and F. D. Cook (Int. J. Syst. Baceteriol. 28:67–393, 1978).

Production of the Antibiotic

*Lysobacter gummosus* A.T.C.C. No. 39472 produces antibiotic EM5487 which possesses activity against yeasts and fungi. To form antibiotic EM5487 according to the preferred method, *Lysobacter gummosus* A.T.C.C. No. 39472 is grown at, or near, room temperature (25° C.) under submerged aerobic conditions in an aqueous nutrient medium containing an assimilable carbohydrate and nitrogen source. The fermentation is carried out until substantial activity is imparted to the medium, usually about 24 to 48 hours, depending upon fermentation conditions.

After the fermentation is completed, the broth is centrifuged to remove the producing organism. The antibiotic is then extracted from the acidified broth supernate with ethyl acetate, back extracted into 5% sodium bicarbonate, and after acidification of the sodium bicarbonate solution to pH 2, is reextracted into ethyl acetate. Alternatively, the whole broth can be acidified with hydrochloric acid and the suspension then centrifuged to pellet the solids. The solids are extracted with acetone, and the acetone extracts are pooled and concentrated in vacuo. The activity in the resulting concentrate, that is diluted with water, is extracted into ethyl acetate, back extracted into 5% sodium bicarbonate and then upon acidification of the bicarbonate solution, extracted into fresh ethyl acetate. Further purification of the antibiotic is achieved by chromatography on silica gel with a chloroform-methanol gradient, followed by chromatography of the active material on Diaion CHP20P with a water-acetone gradient. Final purification is achieved by chromatography on Sephadex LH-20, eluting with methanol.

The following examples further illustrate the preparation of EM5487.

EXAMPLE 1

Yeast extract, peptone, glucose agar slants were seeded with *Lysobacter gummosus* A.T.C.C. No. 39472, incubated overnight at 25° C. and used to inoculate 100 ml portions of an aqueous medium contained in 500 ml cotton-plugged Erlenmeyer flasks. The composition of the germination medium was:

| Medium | Grams |
|---|---|
| Yeast extract | 4 |
| Malt extract | 10 |
| Dextrose | 4 |
| Distilled water to 1 liter | |

The pH was adjusted to 7.3 before sterilization at 121° C. for 15 minutes. The inoculated germination flasks were incubated at 25° C. for approximately 24 hours on a rotary shaker operated at 300 r.p.m. with a 2 inch stroke.

A 1% (v/v) transfer was made from the germination flasks to 100 ml portions of fresh yeast extract, malt extract, dextrose medium as described above. The flasks were incubated at 25° C. for approximately 48 hours, with the same operating conditions as described for the germinator flasks.

At the end of the incubation period, the contents of the flasks were pooled and the pool was centrifuged at 62,500×g to pellet the cells. After separation of cells and supernate, the latter (20 liters), was adjusted to pH 2 with concentrated hydrochloric acid and was subsequently extracted with an equal volume of ethyl acetate. After separation of the phases, the organic layer was washed with water until the pH of the washings was about 4.5 and then concentrated in vacuo to 2.8 liters. The concentrate was extracted twice with 0.5 volume each time of aqueous 5% sodium bicarbonate. The combined aqueous layers were stirred vigorously at room temperature while being adjusted to pH 2 with 6N HCl. The antibiotic was subsequently back-extracted into ethyl acetate (3 liters) which was then washed with water until the pH of the washing was approximately 6. The organic layer was dried over anhydrous $MgSO_4$, filtered and concentrated to dryness in vacuo to yield a residue of 4.5 g of crude antibiotic.

The crude material was dissolved in a small volume of methanol (10 ml) and chloroform (5 ml) and the solution was chromatographed on a silicic acid column (2.5 cm×46 cm) with 2 liters of a linear gradient going from chloroform to chloroform-methanol (1:1), with a flow rate of 3 ml/minute, collecting 12 ml fractions. The active fractions, assayed by paper disc, agar diffusion assay v. *Candida albicans* SC5314 were combined and concentrated in vacuo to dryness, yielding 2.1 g of a yellow solid.

The solid material was dissolved in a minimal volume of a mixture of acetone water (3:1) and chromatographed on a 2.5 cm×28 cm column of Diaion CHP20P*, eluted with 1.2 liters of a linear gradient going from 20% acetone in water to 100% acetone. The flow rate was 3 ml/minute, 12 ml fractions being collected. The active fractions, eluted with approximately 70% aqueous acetone, were combined and evaporated to dryness in vacuo, yielding 600 mg of a yellow solid.
*Diaion CHP20P is macroreticular styrene-divinyl-benzene copolymer beads, Mitsubishi Chemical Company Ltd., Japan.

Further purification was effected by chromatography on a 2.5 cm×110 cm column of Sephadex LH-20*. The eluting solvent was methanol, at a flow rate of 2 ml/minute. The active fractions were combined and the solvents were evaporated in vacuo to give 280 mg of EM5487 as a yellow-orange amorphous solid.
*Sephadex LH-20 is alkylated crosslinked dextran gel beads, Pharmacia Fine Chemicals AB, Uppsala, Sweden The following are phyiscal and chemical properties of antiboitic EM5487:

UV λmax in methanol: 260 nm ($E^{1\%}$ 600), 335 (180).
UV λmax in 0.01N NaOH: 260 nm ($E^{1\%}$ 760), 335 (180).
UV λmax in 0.01N HCl: 269 nm ($E^{1\%}$ 600), 357 (238), 375 (180).

IR(KBr): 3405 broad, 2930, 2895, 2800, 1703, 1655, 1620, 1566 and 1005 $cm^{-1}$.

Molecular Weight: 510 by FAB MS: $(M+H)^+$ m/z 511; $(M-H)^-$ m/z 509.

High resolution mass spectral data on the ion fragment $(M-H)^-$, m/z 509 analyse for $C_{29}H_{37}N_2O_6$.

Elemental analysis: Found C: 64.98; H: 7.46; N: 5.86.

TLC: Silica gel (Merck). $CHCl_3$: MeOH: 0.05M phosphate buffer, pH 2.3 (65:35:10, lower phase), Rf 0:3.
:Opti UP C12** 70% aqueous acetone, Rf 0.3.
Opti UP C12 thin layer reverse phase chromatography plates bonded with dodecyltrichlorosilane, Fluta Chem. Corp., New York :ITLC/SA* $CHCl_3$: MeOH: EtOAc (90:5:2) Rf 0.3.
***Sheets of glass microfibers impregnated with silicic acid for thin layer chromatography, Gelman Instrument Co., Ann Arbor, Mich.

Yeast extract, peptone, glucose agar slants were seeded with *Lysobacter gummosus* A.T.C.C. No. 39472, incubated overnight at 25° C. and used to inoculate 100 ml portions of an aqueous medium contained in 500 ml, cotton-plugged Erlenmeyer flasks. The composition of the germination medium was:

| Medium | Grams |
|---|---|
| Yeast extract | 4 |
| Malt extract | 10 |
| Dextrose | 4 |
| Distilled water to 1 liter | |

The pH was adjusted to 7.3 before sterilization at 121° C. for 15 minutes.

The inoculated germination flasks were incubated at 25° C. for approximately 24 hours on a rotary shaker operated at 300 r.p.m. with a 2 inch throw.

A 1% (v/v) transfer was made from the germination flasks to 50 liters of the same medium as described above contained in a 75 liter Fermatron fermentor (New Brunswick Scientific, Edison, N.J.). The fermentation was allowed to proceed for 28 to 30 hours at 25° C. with an air flow of 50 liters of air/minute and an agitation rate of 200 r.p.m. At the end of the fermentation, the broth was harvested and adjusted to pH 2 by the addition of concentrated HCl. The acidified broth was then centrifuged at 62,500×g to separate the solids and the supernate.

The solids, 375 g wet weight, were suspended in 2.5 liters of acetone and stirred for approximately 30 minutes at ambient temperature. The acetone was collected by filtration through Whatman No. 1 filter paper and the solids again suspended in a fresh portion of acetone (2.5 liters). After stirring, the separation of solids and acetone was again effected and the extraction process repeated once again. The three acetone extracts were combined and concentrated in vacuo to an aqueous slurry (approximately 200 ml). The slurry (pH 4) was diluted by the addition of 200 ml of distilled water and the pH adjusted to 2 by the addition of concentrated HCl. The acidifed slurry was extracted twice with 500 ml portions of ethyl acetate, and the organic phases were retained and combined. This pool was extracted twice with 600 ml portions of 5% aqueous sodium bicarbonate. The aqueous layers were combined and acidified to pH 2 with concentrated HCl. The antibiotic was subsequently reextracted from the acidified aqueous phase with two extractions of 1.5 liters each of fresh ethyl acetate. The combined ethyl acetate extracts were washed with water until the pH of the washing was neutral, concentrated to 500 ml in vacuo, dried over anhydrous MgSO$_4$, filtered to remove any solids and then concentrated in vacuo to a residue (2.35 g).

Biological Activity

Using purified EM5487 as the test compound, two fold agar dilution assays with several Candida species showed the following results:

| Organism | MIC (μg/ml) |
|---|---|
| *Candida albicans* SC*5314 | 3.1 |
| *Candida albicans* SC11422 | 3.1 |
| *Candida albicans* SC12734 (*Bacilysin$^r$*)** | 1.6 |
| *Candida tropicalis* SC8159 | 6.3 |
| *Candida tropicalis* SC2963 (*Amphotericin B$^r$*) | 6.3 |
| *Candida tropicalis* SC9861 (*Amphotericin B$^r$*) | 1.6 |
| *Candida krusei* SC2967 (*Amphotericin B$^r$*) | 3.1 |
| *Candida krusei* SC2969 (*Nystatin$^r$*) | 3.1 |
| *Candida parakrusei* SC2621 | 1.6 |
| *Candida pseudotropicalis* SC11241 | 1.6 |
| *Candida quilliermondii* SC2210 | 6.3 |
| *Candida stellatoidea* SC2211 | 6.3 |
| *Candida glabrata* SC11267 | 3.1 |

*SC refers to an organism from the culture collection of E. R. Squibb & Sons, Inc., Princeton, NEW Jersey
**The designation "(r)" means that the organism is resistant to the antibiotic named within the parenthesis.

Figure 2:
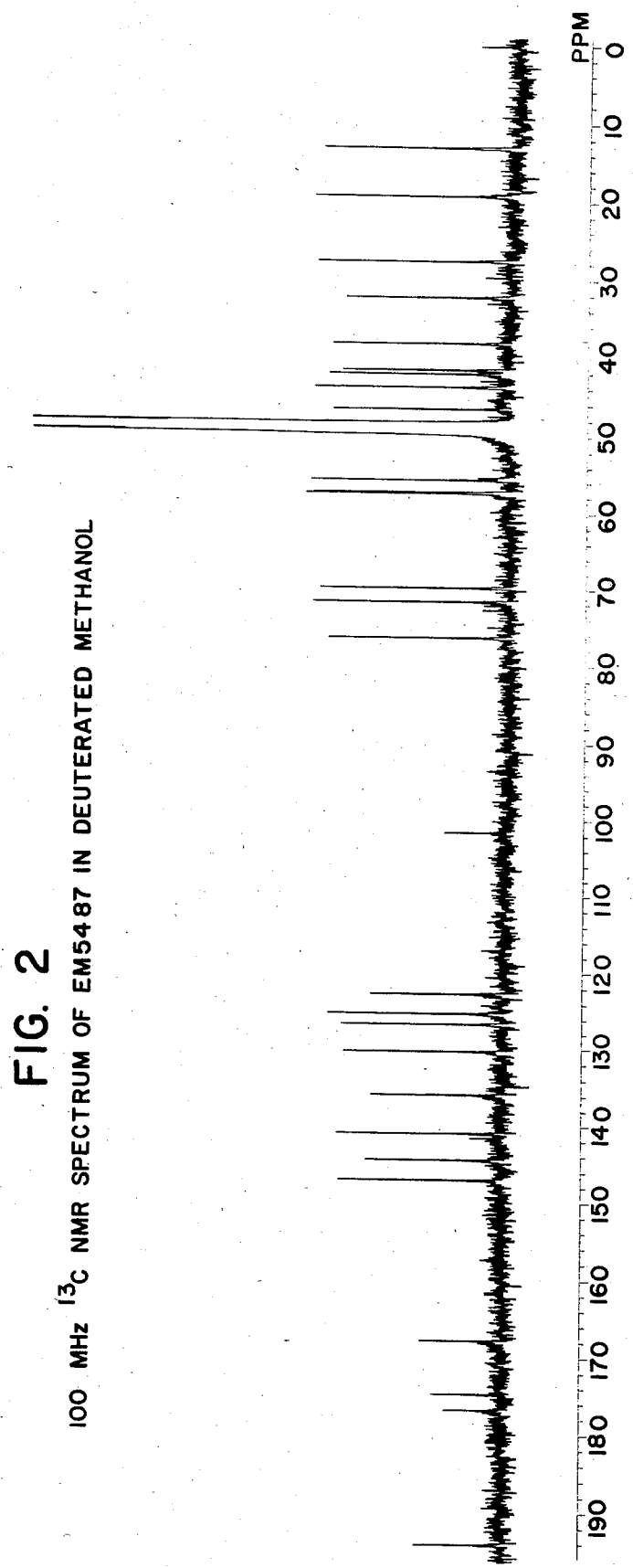
FIG. 2 shows the 100 MHz $^{13}$C NMR spectrum of EM5487 in deuterated methanol.
Figure 3:
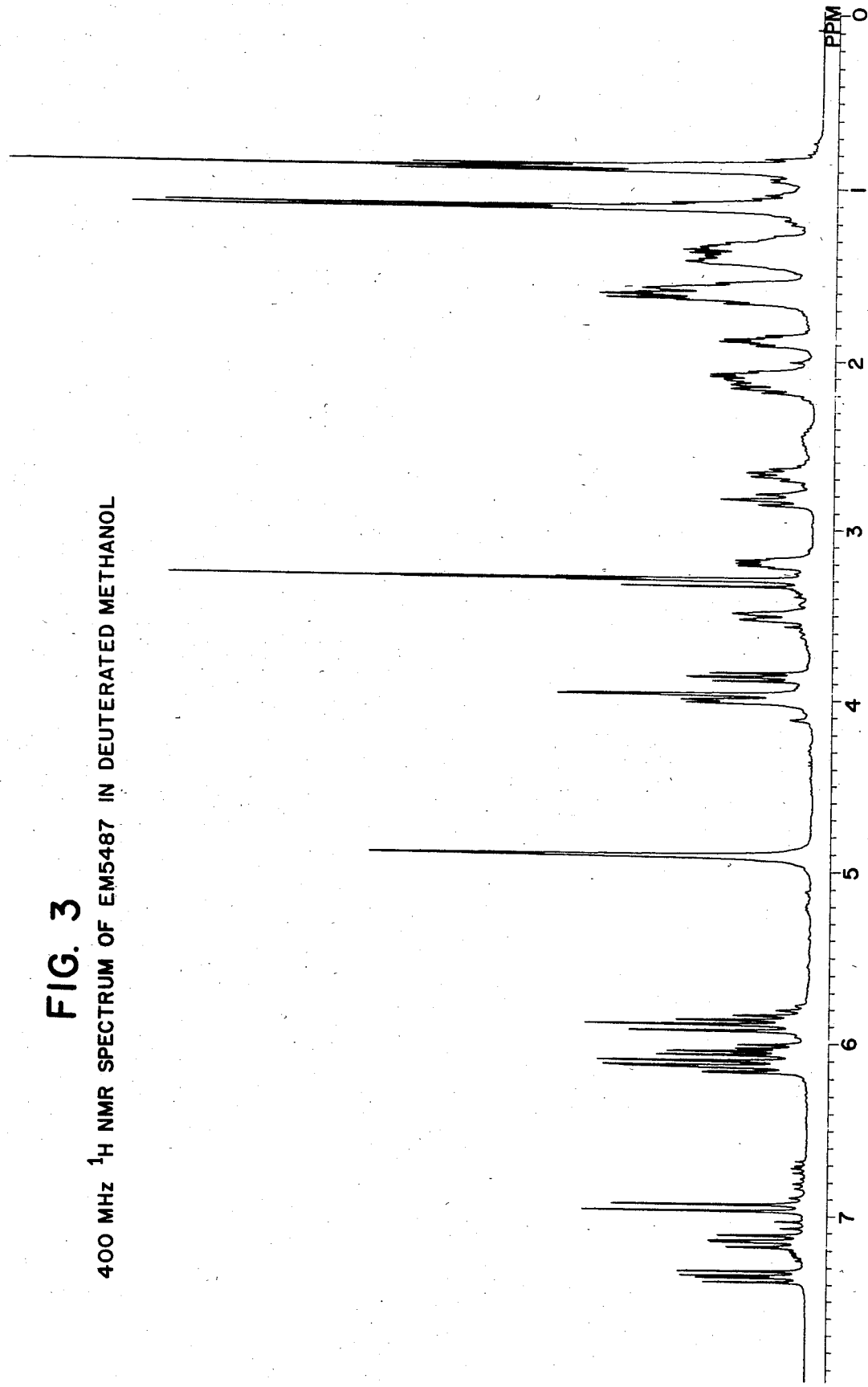
FIG. 3 shows the 400 MHz $^1$H NMR spectrum of EM5487 is deuterated methanol.
Figure 4:
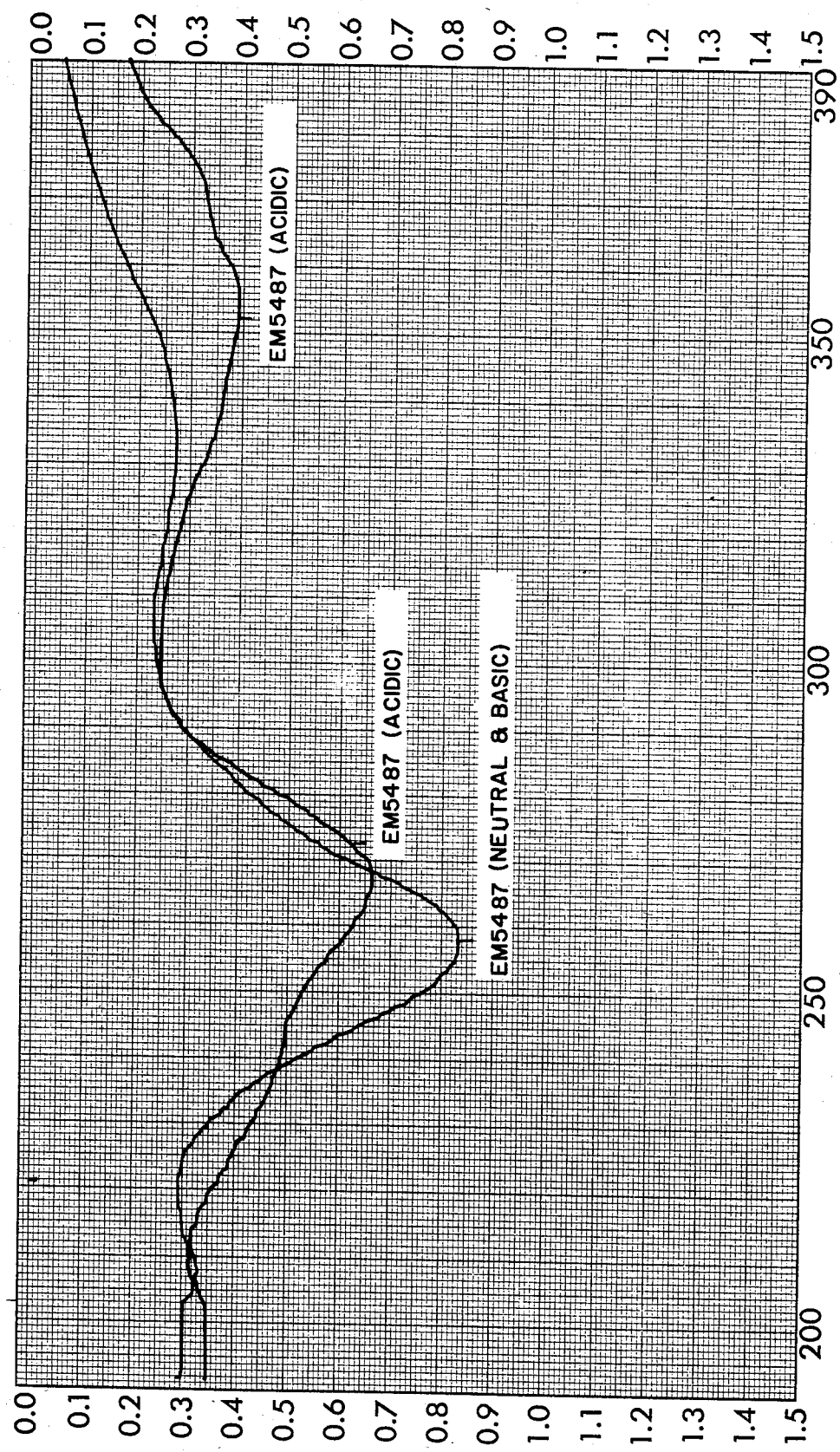
FIG. 4 shows the ultraviolet spectrum of EM5487 in methanol.

What is claimed is:

1. EM5487, having the approximate elemental analysis C, 64.98; H, 7.46; N, 5.86; having the infrared spectrum in potassium bromide shown in FIG. 1; having the 100 MHz $^{13}$C NMR spectrum in deuterated methanol shown in FIG. 2; having the 400 MHz $^1$H NMR spectrum is deuterated methanol shown in FIG. 3; and having the ultraviolet spectrum in methanol shown in FIG. 4.

2. A process for preparing EM5487 which comprises cultivating *Lysobacter gummosus* A.T.C.C. No. 39472 in an aqueous nutrient medium containing an assimilable carbohydrate and nitrogen source under submerged aerobic conditions until substantial EM5487 antibiotic activity is imparted to the medium and isolating the EM5487 antibiotic.

3. A process in accordance with claim 2 wherein the organism is cultivated at about 25° C.

* * * * *